United States Patent [19]

Cooper

[11] Patent Number: 4,931,058

[45] Date of Patent: Jun. 5, 1990

[54] PARALLEL JAW SPRING CLIP AND METHOD OF MAKING SAME

[75] Inventor: Robert P. Cooper, Yorba Linda, Calif.

[73] Assignee: Applied Vascular Devices, Inc., Santa Ana, Calif.

[21] Appl. No.: 394,826

[22] Filed: Aug. 16, 1989

[51] Int. Cl.$^5$ ............................................. A61B 17/12
[52] U.S. Cl. ....................................... 606/158; 24/523
[58] Field of Search .................... 606/120, 157, 158; 251/7; 24/523, 522; 604/250

[56] References Cited

U.S. PATENT DOCUMENTS 3,509,882  9/1967  Blake .
3,510,923  5/1970  Blake .
3,518,993  5/1967  Blake .

Primary Examiner—Michael H. Thaler
Attorney, Agent, or Firm—Limbach, Limbach & Sutton

[57] ABSTRACT

A spring clip including parallel jaws carried by telescopically interengaged carrier members. The jaws are spring biased toward one another by a compression coil spring captured between opposed end caps on the carrier members. One of the carrier members has diametrically aligned slots formed through opposed side walls thereof to enable the other member to passed through said slots and snapped into telescopic receipt within said one member. The end caps are formed integrally with the carrier members. In assembly of the clip, the carrier members are passed into telescopic engagement with the end caps in place and the compression coil spring interposed between the end caps.

13 Claims, 2 Drawing Sheets

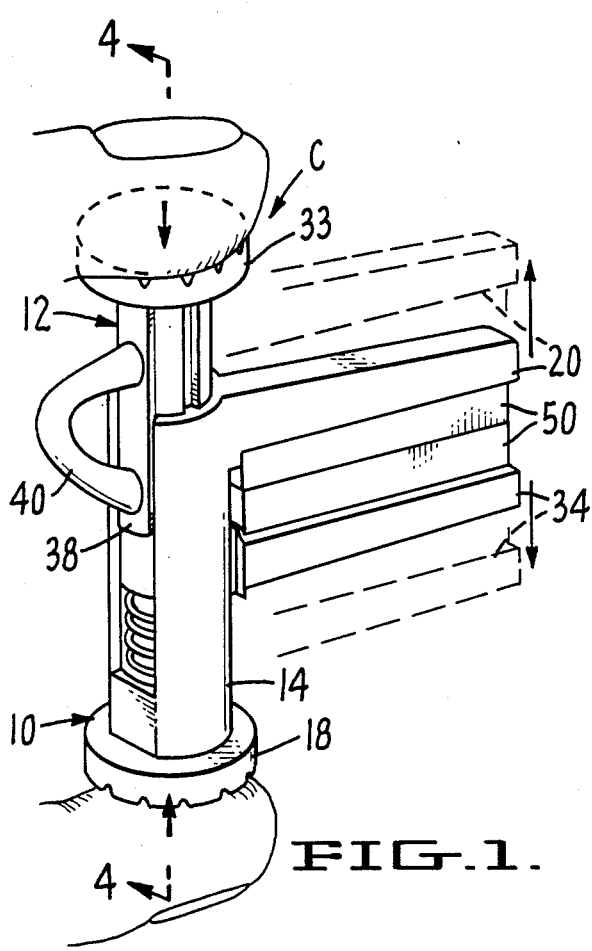
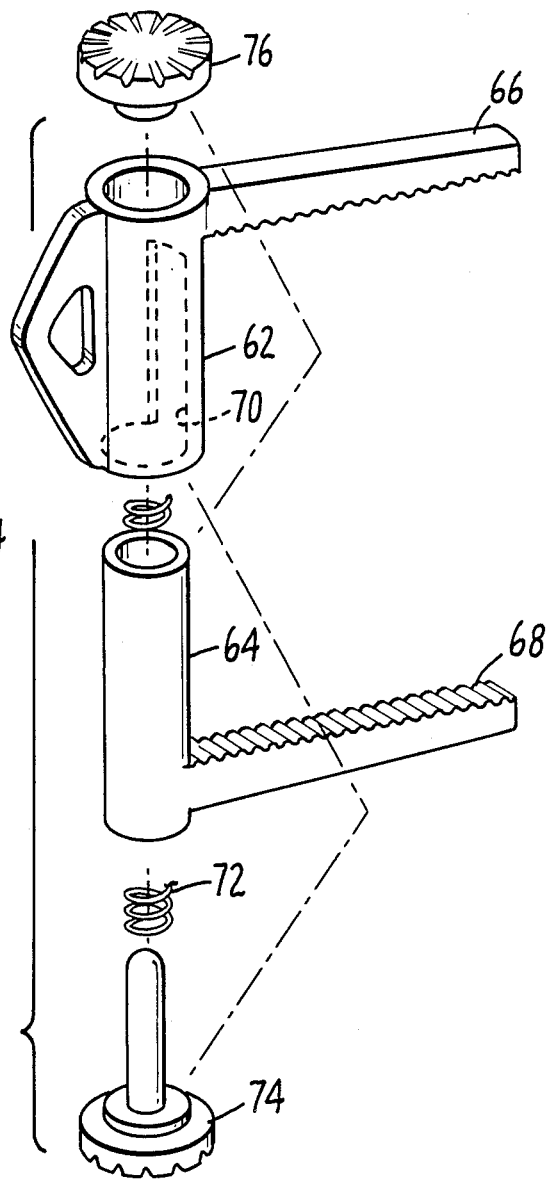
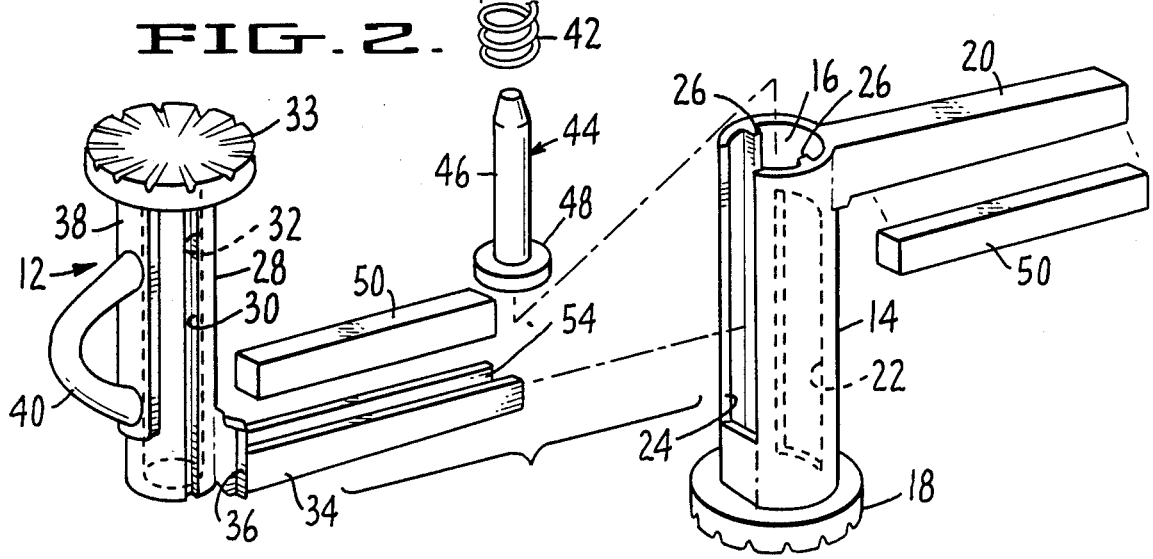
FIG.1.
FIG.3
(PRIOR ART)
FIG.2.

U.S. Patent   Jun. 5, 1990   Sheet 2 of 2   4,931,058
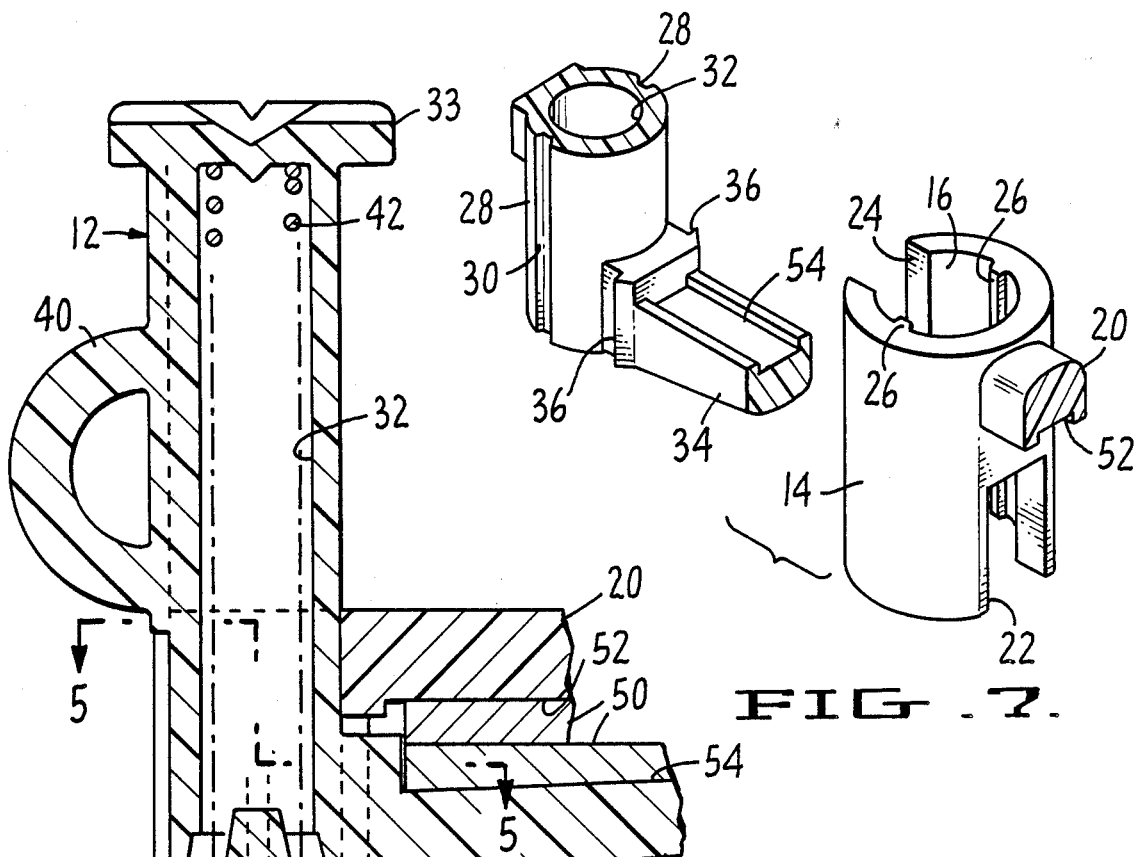
FIG. 4.
FIG. 7.
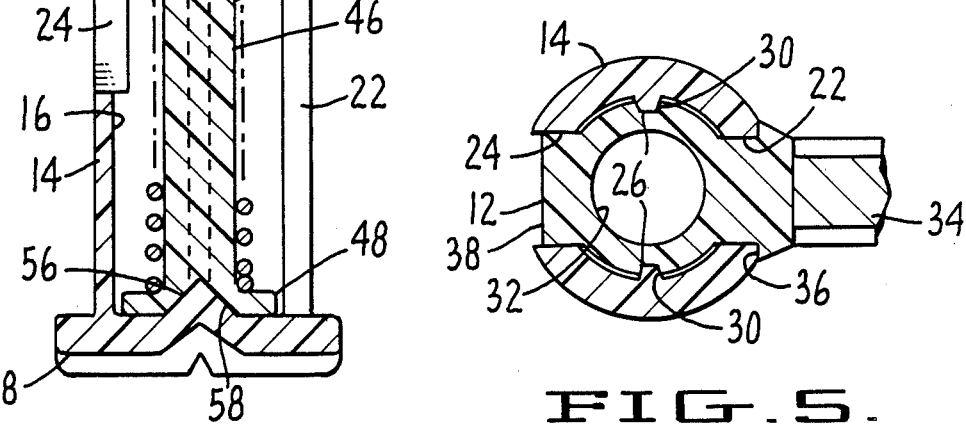
FIG. 5.
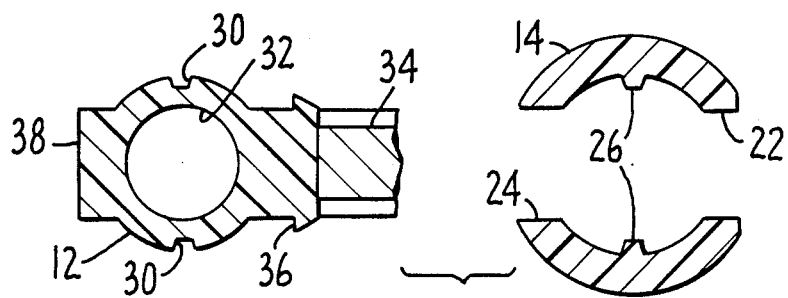
FIG. 6.

PARALLEL JAW SPRING CLIP AND METHOD OF MAKING SAME

BACKGROUND OF THE INVENTION

The present invention relates to an improved parallel jaw spring clip for surgical use and an improved method for assembling such a clip. It is particularly directed to a clip which is of an inexpensive disposable nature and to a method of assembling the clip without employing steps which require that elements of the clip be secured together by adhesion or bonding.

The prior art relating to parallel jaw clips for surgical use is well developed. U.S. Pat. No. 3,509,882 to Blake teaches such a clip employing inner and outer telescopically interengaged elongate carriers with jaws which are resiliently biased towards one another. The clip of that patent, however, requires that during assembly end caps be adhesively secured or bonded to the carriers.

SUMMARY OF THE INVENTION

The clip of the present invention comprises inner and outer telescopically interengaged elongate carriers fabricated of a resilient polymeric material. Each carrier has a generally cylindrical side wall, an elongate passage open at one end and closed at the other end, and a jaw fixed to an extending radially from the carrier adjacent said one end. The outer carrier is provided with diametrically aligned slots which open into the elongate passage therein. One of the slots has closed ends and is disposed intermediate the jaw element and the closed end of the carrier. The other slot opens through the open end of the carrier. In assembly, the inner carrier is passed through the other slot of the outer carrier to direct the jaw element of the inner carrier through the radially aligned slots and snap the inner carrier into telescopic engagement with the passage of the outer carrier. Simultaneously with the passing of the inner carrier laterally through the other slot of the outer carrier, a compression coil spring is interposed between the closed ends of the carriers.

A principal object of the invention is to provide a disposable parallel jaw spring clip for surgical use wherein the elements of the clip may be assembled without the necessity of steps requiring bonding or adherence.

Another object of the invention is to provide such a clip of a simplified construction having a minimum number of parts.

Yet a further object of the invention is to provide such a clip having improved guide elements incorporated into the carriers for the jaw elements.

Still another object of the invention is to provide such a clip incorporating an improved guide element for the coil spring embodied in the clip, which guide element facilitates placement of the spring simultaneously with assembly of the carrier elements into telescopically interengaged relationship.

Yet another object of the invention is to provide such a clip wherein the carrier elements of the clip are disposed in telescopic interengagement by moving one carrier laterally into the other.

These and other objects will become more apparent when viewed in light of the following detailed description and accompanying drawings.

BRIEF DESCRIPTION OF THE DRAWINGS

FIG. 1 is a perspective view of a clamp constructed according to the present invention, with the thumb and forefinger of a human operator shown as they would be placed to open the clamp, and phantom lines illustrating the jaw elements of the clamp in open condition;

FIG. 2 is an exploded-perspective view illustrating how the elements of the inventive clamp are assembled;

FIG. 3 is an exploded-perspective view illustrating the elements of a prior art spring clamp and the manner in which they are assembled;

FIG. 4 is a cross-sectional elevational view taken on the plane designated by line 4—4 on FIG. 1;

FIG. 5 is a cross-sectional view taken on the plane designated by line 5—5 of FIG. 4;

FIG. 6 is a cross-sectional view, with parts thereof broken away, illustrating the elements shown in FIG. 5 in exploded condition as they would appear prior to assembly;

FIG. 7 is a perspective view, with parts thereof broken away, illustrating the elements shown in FIG. 5 in exploded condition as they would appear prior to assembly.

DESCRIPTION OF THE PREFERRED EMBODIMENT

The clamp of the present invention is designated in it's entirety by the letter "C". Its principal elements comprise of first or outer carrier 10 and a second or inner carrier 12, both of which are fabricated of a resilient polymeric material, such as polycarbonate. The outer carrier 10 comprises: a generally cylindrical side wall 14; and an elongate passage 16 extending longitudinally of the carrier and opening through one end thereof (the top end as viewed in FIG. 2), said passage being closed by a cap 18 integrally formed on the end of the carrier opposite said one end; a first jaw element 20 fixed to and extending radially from the side wall 14 adjacent the open end of the carrier; and, radially extending diametrically aligned slots 22 and 24 opening laterally through the side wall 14. The slot 22 has closed ends and is disposed intermediate the cap 18 and jaw element 20. The slot 24 opens through the open end of the carrier. Diametrically opposed ribs 26 extend longitudinally along opposite sides of the passage 16.

The second or inner carrier 12 comprises: a cylindrical body 28 proportioned for slidable receipt within the passage 16; grooves 30 positioned and proportioned to slidable receive the ribs 26; and an elongate passage 32 extending longitudinally of the carrier from an open end (the bottom is viewed in FIG. 2) to a closed cap 33 integrally formed on the carrier; a jaw element 34 fixed to an extending radially from the carrier adjacent the open end thereof; shoulders 36 formed on the jaw element 34 for slidable engagement over the edges of the slot 22; a protrusion 38 integral with the external surface of the cylindrical body 28 and proportioned for slidable receipt within the groove 24; and, an apertured handle 40 fixed to and extending laterally from the protrusion 38.

The remaining elements of the inventive clamp comprise: a compression coil spring 42 proportioned to be received within the passage 32 and engaged between the caps 18 and 33 to force the jaw elements to the closed condition shown in FIG. 1; a guide pin 44 of a length approximately two-thirds the length of the carrier 10, said guide pin having a shaft segment 46 proportioned for slidable receipt within the spring 42 and a head 48 proportioned to be captured between the end of the spring 42 and the cap and, cushions 50 for receipt within grooves 52 and 54 therefore in the carriers 10 and 12, respectively.

The cylindrical body 28 is so proportioned relative to the slot 24 that it may bias the walls of the slot apart and snap through the slot and into slidable receipt within the passage 16, without deforming the carrier 10 beyond its elastic limit. The jaw element 34 is proportioned to slide freely through the slots 22 and 24 during such placement. The ribs 26 are proportioned as to slide over the cylindrical body 28 as the carrier 12 is forced laterally into the carrier 10 through the slot 24 and to snap into the grooves 30.

EXAMPLE

In one example of the invention where the carriers are fabricated of polycarbonate, the principal dimensions of the carriers, in inches, are as follows:

| Outer Carrier (10) | |
| --- | --- |
| Length: | 1.080 |
| O.D.: | .330/.335 |
| I.D.: | .243 |
| Width of closed ended slot (22): | .150/.151 |
| Length of closed ended slot (22): | .750 |
| Width of open ended slot (24): | .150/.151 |
| Length of open ended slot (24): | .687 |
| Inner Carrier (12) | |
| Length: | 1.080 |
| O.D.: | .235 |
| I.D.: | .160 |
| Width between shoulders (36): | .169 |
| Width of protrusion (38): | .148 |
| Length of protrusion (38): | .592 |

ASSEMBLY

In assembly, the cushions 50 are first glued in the grooves 52 and 54 provided therefor in the jaw elements 20 and 34. The guide pin 44 is then placed in the spring 42 and the spring and pin are inserted into the passage 32 of the carrier 12 and compressed. Then the carrier 12 is moved laterally into the slot 24 as the jaw element 34 is directed through the slots 22 and 24. Upon being so directed, the shoulders 36 first snap past the edges of the slot 24 and then the cylindrical body 28 of the carrier 12 snaps through the slot and into the passage 16 of the carrier 10. Ultimately, the shoulders 36 snap past the edges of the slot 22 and the ribs 26 snap into the grooves 30. The spring 42 and pin 44 are then released to permit the spring to force the carrier to the bottom of the passage 16, thus engaging a pointed inner protrusion 56 on the cap 18 with a recess 58 formed in the head 48 of the pin. With the carrier 10 and 12 so assembled and the spring 42 and guide 44 released, the spring functions to spread the carriers as shown in FIGS. 1 and 4, thus forcing the cushions 50 on the jaw elements 20 and 34 into engagement. Forcing the end caps 18 and 33 together functions to spread the jaw elements apart, as depicted by the phantom lines in FIG. 1.

In the assembled condition, the carriers are retained and guided relative to one another and maintained in aligned condition by a combination of features, namely: the smooth complemental cylindrical surfaces on the interior of the passage 16 and the exterior of the body 28; the slidable engagement of the shoulders 36 with the opposite edges of the slot 22; the slidable engagement of the ribs 26 with the grooves 30; and, the slidable engagement of the protrusion 38 with the edges of the slot 24. As a result, the carrier elements 10 and 12 are maintained in axially aligned condition for free telescopic movement relative to one another and the jaw elements 20 and 34 are maintained in aligned condition. All of this is achieved without the necessity of providing separable end caps on the carriers, or means to adhere or bond such caps in place during the assembly process.

DESCRIPTION OF THE PRIOR ART DEVICE

The prior art device shown in FIG. 3 corresponds to that of U.S. Pat. No. 3,509,882. From this figure, it will be seen that the device comprises first and second tubular carriers 62 and 64 having jaw elements 66 and 68, respectively, fixed to an extending laterally therefrom. The carrier 64 is proportioned for slidable receipt within the carrier 62 and an open ended groove 70 is formed in the carrier 62 for slidable receipt of the jaw element 68.

In assembly of the prior art device of FIG. 3, the carrier 64 is telescoped into the carrier 62 and a compression coil spring 72 is extended through a cylindrical passage therefor provided in the carrier 64. Then separate end caps 74 and 76 are forced against the ends of the spring 72 and bonded, or otherwise adhered, to the ends of the carriers 62 and 64, respectively. During this assembly process, that the carriers 62 and 64 are fully nested so that the jaws thereof may engage one another. As a result, the bottom of the carrier 62 is the lower most part of the assembly and the top of the carrier 64 is the upper most part of the assembly. Thus, the cap 74 is secured to the bottom of the carrier 62 and the cap 76 is secured to the top of the carrier 64. During the bonding of the caps, they must be maintained in compression against the force of the spring 72. Once bonding is complete, the spring 72 functions to normally bias the jaws together.

CONCLUSION

From the foregoing description, it is believed apparent that the present invention enables the attainment of the objects initially set forth herein. In particular, it provides a parallel jaw spring clip with carrier members having integrally formed caps which do not need to be bonded or otherwise adhered in place during assembly. It should be understand, however, that the invention is not intended to be limited to the specifics of the embodiment herein and illustrated and described but rather is defined by the accompanying claims.

What is claimed is:

1. An improved parallel jaw spring clip, comprising:
   (a) a first elongate carrier fabricated of a resilient polymeric material, said carrier having:
   a generally cylindrical side wall;
   an elongate passage extending longitudinally thereof, said passage opening through one end of the carrier and being closed by a cap on the end of the carrier opposite said one end;
   a first jaw element fixed to and extending radially from the side wall adjacent said one end;
   diametrically aligned slots opening laterally through said side wall, one of said slots having closed ends and being disposed intermediate the cap and the jaw element, the other of said slots opening through said one end of the carrier and terminating in a closed end adjacent the cap;

(b) a second elongate carrier telescopically received within the passage of the first carrier for longitudinal movement relative thereto, said carrier being generally cylindrical and so proportioned relative to said other slot that said second carrier may be passed laterally through said other slot to resiliently bias the wall of the first carrier apart to enable the second carrier to snap into telescopic engagement within the first carrier, said second carrier having:

an elongate passage extending longitudinally thereof, said passage opening through one end of the carrier and being closed by a cap on the end of the carrier opposite said one end;

a second jaw element fixed to and extending radially from the end of the second carrier adjacent said one end thereof, said second jaw element extending through said one slot for movement toward and away from the first jaw element responsive to longitudinal movement of the first and second carriers relative to one another;

(c) resilient means to normally bias the first and second carrier for telescopic movement relative to one another in a direction forcing the first and second jaw elements toward one another.

2. A spring clip according to claim 1 wherein the resilient means comprises a compression coil spring engaged between the caps of the carriers.

3. A spring clip according to claim 2 wherein said spring is received within the elongate passages of the first and second carriers, further comprising a guide pin extending slidably through a portion of the length of the coil spring, said pin being separate from the carriers and having a head captured between the spring and the cap on the end of the second carrier.

4. A spring clip according to claim 1 further comprising a protrusion on the second carrier proportioned for slidable engagement within said other slot of the first carrier.

5. A spring clip according to claim 4 further comprising an apertured handle fixed to and extending laterally from the protrusion.

6. A spring clip according to claim 1, further comprising ribs formed on the passage in the first carrier and grooves formed in the second carrier for slidable receipt of said ribs to guide the carriers for telescopic movement relative to one another.

7. A spring clip according to claim 1 or 6, further comprising a shoulder formed on the jaw element of the second carrier, said shoulder being proportioned to snap through said one slot of the first carrier and engage to either side thereof to guide the carriers for telescopic movement relative to one another.

8. In a parallel jaw spring clip of the type comprising:
(a) inner and outer telescopically interengaged elongate carriers fabricated of a resilient polymeric material, each of said carriers having:

a generally cylindrical side wall;

an elongate passage extending longitudinally thereof, said passage opening through one end of the carrier and being closed by a cap on the end of the carrier opposite said one end;

a jaw element fixed to and extending radially from the side wall of the carrier adjacent said one end thereof;

(b) resilient means to normally bias the inner and outer carriers for telescopic movement relative to one another in a direction forcing the first and second jaw elements toward one another;

an improved method for assembling the carriers into telescopic relationship, comprising:

providing the outer carrier with diametrically aligned slots opening laterally through the side wall thereof, one of said slots having closed ends and being disposed intermediate the cap and the jaw element of the outer carrier, the other of said slots opening through said one end of the outer carrier and terminating in a closed end adjacent the cap of the outer carrier;

passing the inner carrier laterally through said other slot of the outer carrier to direct the jaw element of the inner carrier through the radially aligned slots of the outer carrier and resiliently bias the wall of the outer carrier apart to snap the inner carrier into telescopic engagement with the passage of the outer carrier; and, simultaneously with the passing of the inner carrier laterally through said other slot of the outer carrier, interposing a compression coil spring between the caps on the ends of the carriers.

9. An improved method according to claim 8, further comprising providing a guide pin within a portion of the length of coil spring and positioning said pin within the spring simultaneously with the interposition of the spring between the caps on the ends of the carriers.

10. An improved method according to claim 8, further comprising providing a protrusion on the inner carrier proportioned for slidable receipt within the other slot of the outer carrier when the carriers are telescopically interengaged.

11. An improved method according to claim 10, further comprising providing an apertured handle fixed to and extending laterally from the protrusion.

12. An improved method according to claim 8, further comprising providing ribs on the passage of the outer carrier and grooves in the passage of the inner carrier for slidable receipt of the ribs to guide the carriers for telescopic movement relative to one another.

13. An improved method according to claim 8 or 12, further comprising providing a shoulder on the jaw element of the inner carrier, said shoulder being proportioned to snap through said one slot of the outer carrier and engage to either side thereof to guide the carriers for telescopic movement relative to one another.

* * * * *